United States Patent [19]
Dorfman et al.

[11] Patent Number: 5,728,465
[45] Date of Patent: *Mar. 17, 1998

[54] DIAMOND-LIKE NANOCOMPOSITE CORROSION RESISTANT COATINGS

[75] Inventors: Veniamin F. Dorfman, Stony Brook; Arvind Goel, Buffalo, both of N.Y.

[73] Assignee: Advanced Refractory Technologies, Inc., Buffalo, N.Y.

[*] Notice: The term of this patent shall not extend beyond the expiration date of Pat. No. 5,718,976.

[21] Appl. No.: 472,552

[22] Filed: Jun. 7, 1995

Related U.S. Application Data

[60] Continuation-in-part of Ser. No. 471,401, Jun. 6, 1995, which is a division of Ser. No. 249,167, May 25, 1994, Pat. No. 5,466,431, which is a division of Ser. No. 695,552, May 3, 1991, Pat. No. 5,352,493.

[51] Int. Cl.$^6$ ........................................... B32B 9/04
[52] U.S. Cl. ........................ 428/408; 428/446; 428/697; 428/698; 428/699
[58] Field of Search ........................ 428/408, 698, 428/446, 697, 699

[56] References Cited

U.S. PATENT DOCUMENTS

| | | |
|---|---|---|
| 4,191,735 | 3/1980 | Nelson et al. |
| 4,783,368 | 11/1988 | Yamamoto et al. |
| 4,816,291 | 3/1989 | Desphandey et al. |
| 4,822,466 | 4/1989 | Rabalais et al. |
| 4,842,937 | 6/1989 | Meyer et al. |
| 4,877,677 | 10/1989 | Hirocki et al. |
| 4,897,829 | 1/1990 | Ikoma et al. |
| 4,915,977 | 4/1990 | Okamoto et al. |
| 4,948,388 | 8/1990 | Ringwood. |
| 4,960,643 | 10/1990 | Lemelson. |
| 4,961,958 | 10/1990 | Desphandey et al. |
| 4,980,021 | 12/1990 | Kitamura et al. |
| 4,985,051 | 1/1991 | Ringwood. |
| 4,992,298 | 2/1991 | Deutchman et al. |
| 5,002,899 | 3/1991 | Geis et al. |
| 5,040,501 | 8/1991 | Lemelson. |
| 5,055,318 | 10/1991 | Deutchman et al. |
| 5,064,801 | 11/1991 | Juntgen et al. |
| 5,068,148 | 11/1991 | Nakahara et al. |
| 5,077,103 | 12/1991 | Wagner et al. |

(List continued on next page.)

FOREIGN PATENT DOCUMENTS 2 158 086  3/1985  United Kingdom.

OTHER PUBLICATIONS

Dorfman, "Diamond–Like Nanocomposites (DLN)", Thin Solid Films, 267–273:212 (1992).
R. d'Agostino, ed., "Plasma Deposition, Treatment and Etching of Polymers", Academic Press, San Diego, 1990.
Dorfman, V.F., et al., Sov. Phys. Dokl., 28 (1983) 743 (English Abstract).
Dorfman, V., "Synthetics of Solid State Structure", Metallurgia, Moscow (1986).
Dorfman, V., et al. Diamond Films '90, Proc. 1st European Conf. on Diamond and Diamond–Like Carbon Coatings, Crans-Montana (1990).
Weissmantel et al. J. Vac. Sci. Technol. vol. A4, 2892.
Dorfman, et al. J. Tech. Phys. Lett., 14:1033 (1988).
Ageev, "Light Induced Variations of Optical Properties of Diamond–Like Films", Surface and Coating Technologies, 47:269–278 (1991).

*Primary Examiner*—Archene Turner
*Attorney, Agent, or Firm*—Nixon, Hargrave, Devans & Doyle LLP

[57] ABSTRACT

A method for inhibiting corrosion of a substrate by applying to a substrate a corrosion resistant coating comprising a diamond-like solid state material having interpenetrating atomic scale networks of class of diamond-like solid state materials formed from interpenetrating networks comprising a first network of carbon in a diamond-like carbon network stabilized by hydrogen, a silicon network stabilized by oxygen, and optionally at least one network made from dopant elements or dopant compounds containing elements from groups 1–7b and 8 of the periodic table.

9 Claims, 5 Drawing Sheets

U.S. PATENT DOCUMENTS

| | | |
|---|---|---|
| 5,087,434 | 2/1992 | Frenklach et al. |
| 5,094,915 | 3/1992 | Subramaniam |
| 5,100,424 | 3/1992 | Jang et al. |
| 5,101,288 | 3/1992 | Ohta et al. |
| 5,110,577 | 5/1992 | Tamor et al. |
| 5,135,808 | 8/1992 | Kimock et al. |
| 5,137,784 | 8/1992 | Suzuki et al. |
| 5,142,390 | 8/1992 | Ohta et al. |
| 5,158,828 | 10/1992 | Sudani et al. |
| 5,169,579 | 12/1992 | Marcus et al. |
| 5,171,732 | 12/1992 | Hed |
| 5,174,983 | 12/1992 | Snail |
| 5,177,299 | 1/1993 | Kondo et al. |
| 5,183,602 | 2/1993 | Raj et al. |
| 5,190,807 | 3/1993 | Kimock et al. |
| 5,198,285 | 3/1993 | Arai et al. |
| 5,202,571 | 4/1993 | Hirabayashi et al. |
| 5,206,083 | 4/1993 | Raj et al. |
| 5,210,430 | 5/1993 | Taniguchi et al. |
| 5,219,769 | 6/1993 | Yonehara et al. |
| 5,243,199 | 9/1993 | Shiomi et al. |
| 5,256,483 | 10/1993 | Yamazaki et al. |
| 5,352,493 | 10/1994 | Dorfman et al. |

UNCOATED
ALUMINUM
2000 ml

DLN/Al 2000 ml

Hf-DLN/Al 1000ml

UNCOATED STEEL
2000 ml

DLN/STEEL
2000 ml

Hf-DLN/STEEL
3000 ml 5,728,465

DIAMOND-LIKE NANOCOMPOSITE CORROSION RESISTANT COATINGS

This application is a continuation-in-part of U.S. patent application Ser. No. 08/471,401, filed Jun. 6, 1995 as a divisional of U.S. patent application Ser. No. 08/249,167, filed May 25, 1994 (now issued as U.S. Pat. No. 5,466,431), which is a divisional of U.S. patent application Ser. No. 07/695,552, filed May 3, 1991 (now issued as U.S. Pat. No. 5,352,493).

This invention was developed with government funding under Department of Defense Contract No. N60921-93-C-A356. The U.S. Government may have certain rights.

BACKGROUND OF THE INVENTION

Field of the Invention

The present invention relates to corrosion and erosion resistant coatings made from diamond-like materials.

The corrosion of parts and surfaces remains a significant problem in the world. The annual estimated cost of corrosion and of protecting against corrosion in the United States exceeds 8 billion dollars. Materials used as coatings to inhibit corrosion are known. However, the problems of corrosion persist, and an ideal, effective corrosion inhibiting coating for metals and non-metals alike has not been found.

Corrosion eventually results in the degradation of metals or alloys due to reaction with the environment. Attack of non-metals, such as polymers can also occur by exposure to organic solvents as well as environmental conditions. Corrosive forces are often intensified at or near bodies of salt-containing water. Such corrosion, over time degrades substrates used for, for example, heavy structural metals, highly sensitive electronic equipment, decorative metals and metal plating, etc. which may be found in, for example heavy equipment, automobiles, planes, trucks, ships, etc. Many coatings have been tried on metals and other substrates to resist environmental deterioration, such as corrosion and erosion. However, none of the known coatings successfully inhibit such corrosive forces.

Metal-based coatings such as steel, zinc, aluminum, chromium, nickel, alloys, cadmium, tantalum, palladium, boron, silicon, copper, gallium, rhenium, alloys thereof, etc. have demonstrated corrosion resistance to salts and are used in many industries to provide corrosion inhibiting coatings. However, coatings made from these materials are generally suitable only for metallic substrates and further display low corrosion resistance in acidic environments.

Silicate based coatings are known to be resistant to air, acid, alkali, and gases at elevated temperatures. However, coatings made from silicates are not particularly strong materials and are therefore vulnerable to erosion.

Certain ceramic materials used as coatings have displayed good corrosion resistance. However, ceramics are brittle and subject to failure. Coatings made from ceramics also display adhesion problems and thermal shock failure.

Polymeric coatings offer good corrosion resistance and have good abrasion resistance. However, polymeric coatings may degrade due to exposure to UV radiation through exposure to sunlight. Further, temperature limitations may lead to blister formation and can cause gross failure and delamination from the substrate.

Organic coatings offer good corrosion resistance, especially rust protection. However, organic coatings have low abrasion resistance and temperature limitations.

SUMMARY OF THE INVENTION

The present invention is directed to corrosion and erosion resistant coatings made from a class of diamond-like solid state materials which can be "tuned" or predictably and desirably altered by manipulating the amounts of substituent to result in the best combination of properties to offer maximum corrosion and erosion resistance to the coated substrates.

According to one feature, the present invention is directed to corrosion and erosion resistant coatings and films made from a class of diamond-like solid state materials formed from interpenetrating networks comprising a first network of carbon in a diamond-like carbon network stabilized by hydrogen, a silicon network stabilized by oxygen and, optionally, at least one network of dopant elements, or dopant compounds containing elements from groups 1–7b and 8 of the periodic table.

According to a further feature, the present invention is directed to a method for inhibiting corrosion of substrates comprising applying to said substrates a coating made from a class of diamond-like solid-state material having interpenetrating atomic scale networks of carbon in a diamond-like carbon network stabilized by hydrogen, a glass-like silicon network stabilized by oxygen, and optionally at least one additional network of dopant elements or dopant compounds containing elements from groups 1–7b and 8 of the periodic table.

According to still a further feature, the present invention is directed to a corrosion resistant material comprising a substrate and a coating applied to the substrate, said coating made from a class of diamond-like solid-state material having interpenetrating atomic scale networks of carbon in a diamond-like carbon network stabilized by hydrogen, a glass-like silicon network stabilized by oxygen, and optionally at least one additional network of dopant elements or compounds containing elements selected from the group consisting of elements from groups 1–7b and 8 of the periodic table.

DETAILED DESCRIPTION OF THE INVENTION

Figure 1A:
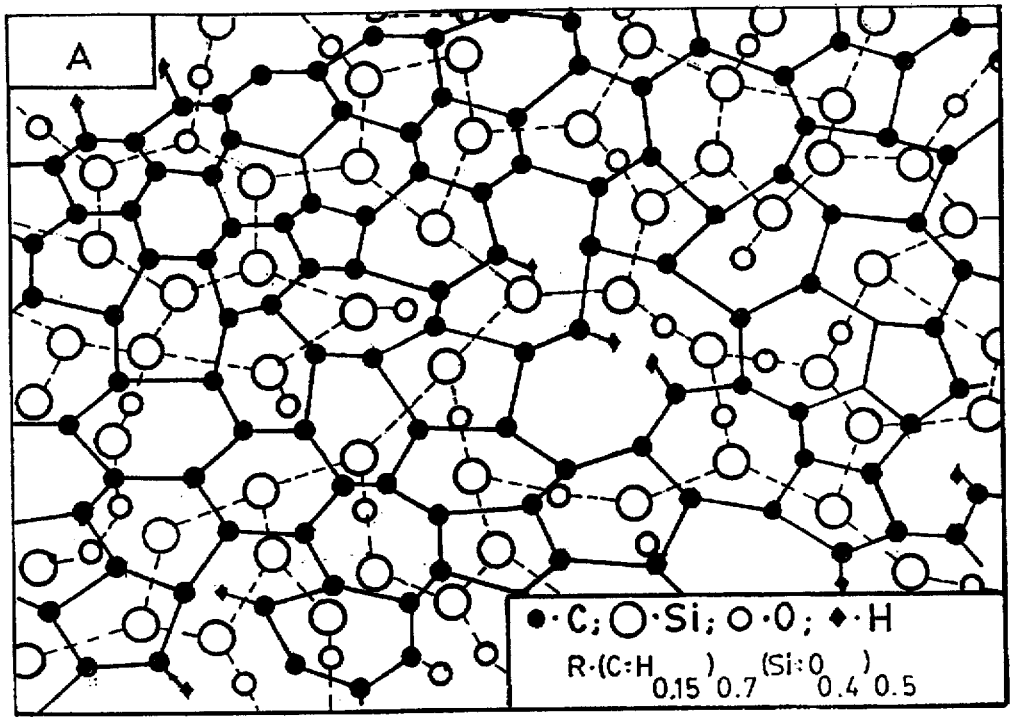
FIG. 1 is a schematic diagram showing the principle microstructure of two-network (A), intermediate (B), and three-network (C) nanocomposites.

The present invention relates to corrosion resistant coatings and films made from a class of diamond-like materials having interpenetrating atomic scale networks of carbon in a diamond-like carbon network stabilized by hydrogen, a glass-like silicon network stabilized by oxygen, and optionally at least one network of dopant elements or dopant compounds, and the use of such materials as protective coatings, especially coatings that are resistant to corrosion and erosion, for example, as a result of environmental exposure to water, salt and sand, etc.

For the purposes of this application, corrosion is defined as the electrochemical degradation of metals or alloys due to reaction with their environment, which is accelerated by the presence of acids or bases. In general, the corrodibility of a metal or alloy depends upon its position in the activity series. Corrosion products often take the form of metallic oxides or halides. For example, sodium chloride, or salt, in the air at locations near the sea is strongly corrosive, especially at temperatures above 21° C. In addition, corrosion may be considered to be the degradation of non-metal substrates by exposure to natural environmental conditions as well as exposure to organic materials.

In addition to the corrosion-resistant properties of the coatings of the present invention, the coatings are strong and erosion resistant, such as to chemicals, abrasion, or ablation while also being highly thermally stable. The coatings would therefore be impervious to biological or chemical attack and highly resistant to incident laser or other radiation. The resistance of the coatings of the present invention to erosion, reduces the possibility of for example, physical chipping. This results in the surface of the substrate being less likely to exposure to environmental corrosive forces. The coatings have excellent adherence to the substrate and are resistant to thermal shock and elevated temperatures beyond those known to erode known diamond-like coatings.

The fundamental structure of the preferred corrosion and erosion resistant atomic scale diamond-like nanocomposites (DLNs) used to coat the selected substrates is comprised of two or more self-stabilized random networks, each stabilized chemically by additional atomic species, while both networks also structurally stabilize each other. An example of a material with such a structure is the diamond-like nanocomposite (DLN) which is the subject of U.S. Pat. No. 5,352,493 and U.S. Ser. No. 08/249,167 filed May 24, 1994.

In the DLN, a random carbon network, mainly in the form of $sp^3$ "diamond-like" bonds is chemically stabilized by hydrogen atoms, and a glass-like silicon network is chemically stabilized by oxygen atoms, resulting in a purely amorphous structure. "Amorphous" as used herein refers to a random structure or arrangement of atoms in a solid state that results in no long range regular ordering, and lacks crystallinity or granularity. The DLN materials have an amorphous structure and do not contain clusters greater than 10 Angstroms. This absence of clusters at the atomic scale is a key characteristic of the DLN coatings of the present invention. Clusters can destroy amorphous nature of the structure, and can serve as active centers of degradation.

Therefore, the DLNs contain no clusters or ordering greater than that defined by one-third the radius of the coordination sphere. This structure has been confirmed via electron projection methods, scanning tunneling microscopy, atomic force microscopy, glancing x-ray and electron diffraction techniques and high resolution transmission electron microscopy (TEM). Cluster formation is prevented in the sources, in the primary plasma, in the chamber space, and during film growth.

Figure 1B:
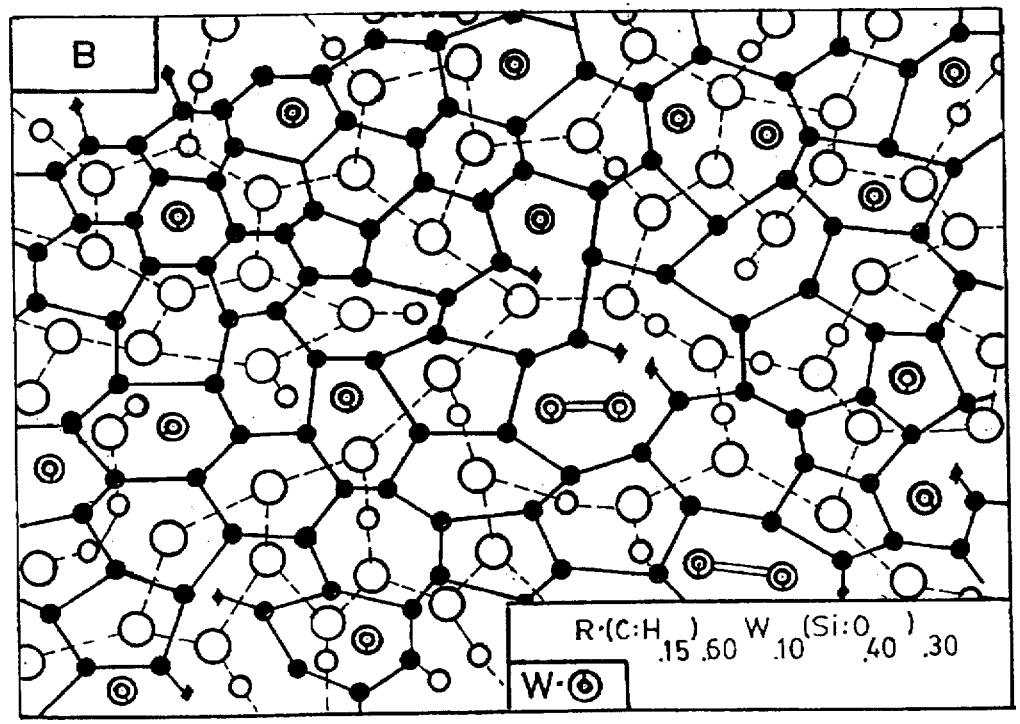
Figure 1C:
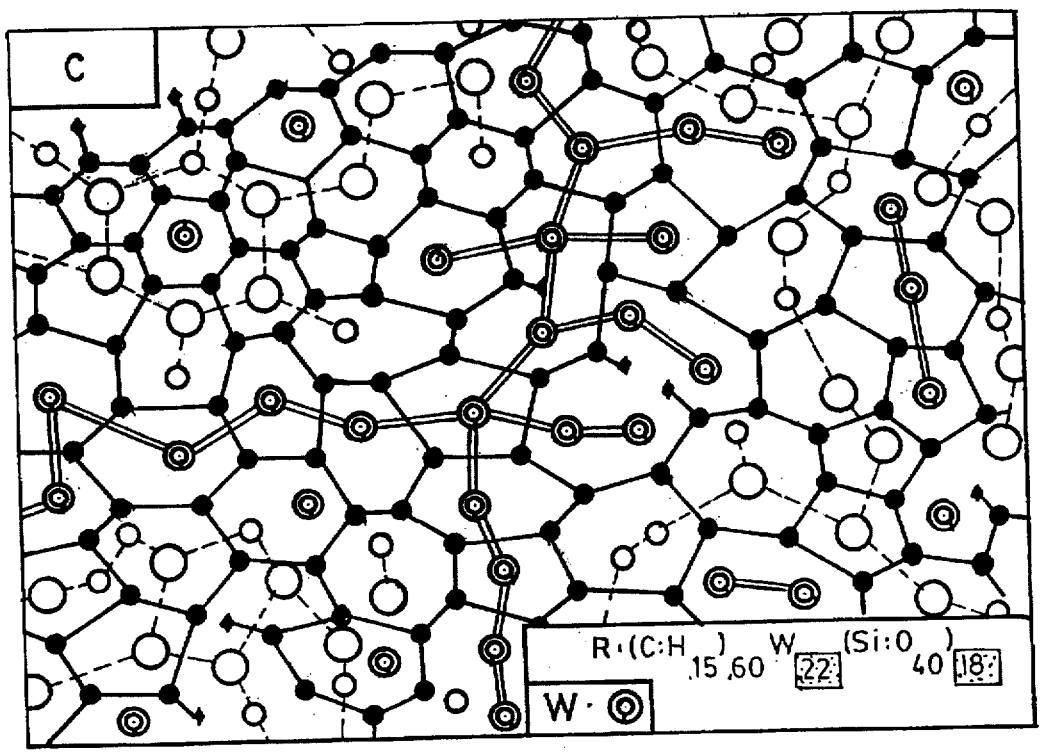

The atomic structure of the class of diamond-like nanocomposite (DLN) solid state materials of the present invention is shown in FIG. 1(A). The materials may have one or more separate disordered networks of dopants, as shown in FIG. 1(B) and 1(C). The dopants may be any one or a combination of the transition metals and non-metals of the groups 1–7b and 8 of the periodic table, and all three types of networks (C—H; Si—O and the dopant network, Me—Me) are bonded to each other predominantly by weak chemical bonds. The network elements other than the C—H network may be referred to as alloying elements. Further, silicon and oxygen atoms may also be used in the dopant networks with other elements and compounds.

The DLN coatings of the present invention may comprise a two component network: the diamond-like carbon-hydrogen network interpenetrated with the glass-like silicon-oxygen network. A three component network may also be used comprising the Si—O and C—H networks with one or more dopant networks, with the dopants being interspersed with the previously mentioned two interpenetrating networks. In this instance three or more interpenetrating networks will be present in the DLN to form a so-called Me-DLN (metal-diamond-like nanocomposite) network. It is understood that non-metal dopant networks, may be incorporated as the optionally present dopant networks interpenetrating the C—H and Si—O networks.

The three networks (C—H matrix, Si—O matrix and a dopant matrix) are bonded to one another mainly by weak chemical bonds. Carbide formation can be prevented even at metal concentrations as high as 50% (verified using Auger electron spectroscopy, electron spectroscopy for chemical analysis (ESCA), extended x-ray absorption fine structure spectroscopy (EXAFS) and Fourier transform infrared spectroscopy (FTIR) can be achieved. Again, the properties of these materials can be varied over wide ranges depending on the dopant and the concentration selected, as well as the deposition technique and parameters. As already mentioned, the structure of these composites can be tailored at the molecular level. Therefore, unique electrical, optical, and other desirable solid state properties with desired mechanical strength, hardness and chemical resistance can be imparted on the DLN coatings.

Preferred dopant elements to be used in the Me-DLN network, and which are particularly effective for use as dopants in a corrosion-resistant Me-DLN coating are B, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag and Au; with W, Cr, Zr, Ti and Hf being preferred. Preferred compounds which may be used as dopants include TiN, BN, AlN, ZrN and CrN with TiN, AlN and CrN being most preferred.

The carbon content in the diamond-like nanocomposite is greater than about 40 atomic % of the DLN. Although the DLN may theoretically be prepared without any hydrogen, the hydrogen content is preferably at least about 1 atomic % and up to about 40 atomic % of the carbon concentration. The sum of the silicon, oxygen and dopant elements and dopant containing compounds is greater than about 2 atomic % of the DLN. In one preferred embodiment, the ratio of carbon to silicon atoms is from from about 2:1 to about 8:1, hydrogen to carbon atoms is about 0.01:1 to about 0.4:1, silicon to oxygen atoms is about 0.5:1 to about 3:1, and dopant to carbon atoms is about 0:1 to about 1.5:1. Therefore, in the DLN network, for every 1 part carbon, there is from about 0.01 to about 0.4 parts hydrogen, from about 0.125 to about 0.5 parts silicon, and from about 0.0375 to about 1.0 parts oxygen. In such a scheme, if a third dopant network were present, for every 1 part carbon, there would be from about 0.01 to about 1.5 parts dopants depending upon the desired characteristics to be imparted to the Me-DLN network.

The low intrinsic stress found in the DLNs contributes to their corrosion resistance properties. A coating must not only be unreactive to a corrosive agent, but should also act as a barrier layer, preventing contact between the corrosive agent and the protected substrate. DLC films typically possess high intrinsic stresses, and as a result usually suffer from pin holes and overall porosity. Due to the comparatively low stress present in DLN films and coatings, these coatings are pore-free, and therefore resist chemical attack and permeation.

The presence of the glass-like silicon network, stabilized by oxygen, serves to prevent the growth of graphitic carbon at high temperatures, to prevent metal cluster formation in metal-containing three-network nanocomposites, and reduce the internal stress in the nanocomposite structure and thereby enhance the adhesion to substrates. This appears to lead to superior adherence of the DLNs of the present invention to the substrate material.

As already mentioned, to improve adherence of coatings, DLC coatings often require an intermediate layer between the substrate and the DLC coating. Often, if the DLC coatings are too thick, delamination occurs. Surprisingly, with the DLN coatings of the present invention, adherence is so good that an interlayer is not required. As a result, the DNL coating may be applied directly to the substrate, and more thickly without risking delamination from the substrate. The ability to apply a thicker layer of DLN coating results from the low intrinsic stress due to the Si—O network, and is believed to contribute to the superior erosion resistance of the DLN-coated substrates.

As already mentioned, corrosion is exacerbated by saltwater. Naval weapons and munitions face specific problems. Naval guns, for example, experience not only severely corrosive elements (e.g. seawater, salt spray, salt mist, etc.) but also severe thermal stresses and thermal shock environments during their operation. A lack of adequate mechanical material strength at elevated temperatures is further aggravated by severe recoil forces during operation. The corrosive effect of the salt vapors in the environment may further contribute to deteriorating performance levels. Weapons, munitions and munitions casings can also be adversely affected due to environmental corrosion and thermal stress. Thus the advanced machine guns, for example, M60, M16, 50 caliber, 25 mm chainguns, 155 mm artillery, 120 mm tank guns, Mark 19 munitions, etc. all exhibit corrosion problems.

Other shipboard equipment is also subject to corrosion. Lubrication is often required to help retard corrosion. However, lubricants have many disadvantages, including the need for constant re-application and removal. These lubricants can also contribute to machine fouling, and often deteriorate, or perform poorly at elevated temperatures. With the current lack of adequate munition and weaponry corrosion protection, replacement of corroded weaponry is often the only safe option. Such replacement is wasteful and expensive.

The corrosion resistant DLN coatings of the present invention may be used in such applications as mentioned above as alternative approach to lubrication, painting, or other means presently used to inhibit corrosion.

Erosion is also a destructive force to both metal and non-metal substrates. For example, plastic and ceramic surfaces on both stationary and moving objects must often endure harsh environmental effects, including erosion. Erosion is encountered by substrates which are exposed to particle impact at such velocity that the substrate surface is impacted adversely, such as by physical pitting or chipping. Such erosion may take place on stationary objects exposed to high winds, or objects which themselves travel at high velocities. For example, airplane or missile windows often show the signs of erosion due to impact at very high speeds with, for example, dirt and dust particles.

The logistical costs of maintaining equipment prone to corrosion are therefore high, and include continual coating, lubrication, maintenance, support and labor. A resilient, low-cost, highly durable, highly adherent and hard coating which is also highly resistant to corrosion, erosion and thermal stress would be highly advantageous.

Components used for semiconductor wafer fabrication processes, such as wafer boats, process tubes, paddles, gas diffusion plates and liner tubes, etc. must withstand the severe and corrosive effects of cleaning or etching agents such as fluoride gases in a plasma environment. The high temperature combined with the need for corrosion resistance, contamination control, thermal shock, and dielectric strength provides an environment to which not many known materials are well-suited. Anodized aluminum, siliconized silicon carbide, recrystallized quartz and other such materials are currently used, however each alternative suffers from either high cost, short life, environmental impact or other such problems.

The DLN coatings of the present invention solve these above-listed and other problems since their characteristics may be "tuned", or selectively altered according to the desired application. Such "tuning" is accomplished by incrementally altering the particular dopant as well as the dopant concentration. The DLNs may also have their properties altered when no dopants are included. Such changes in properties in the two-network system can be achieved by altering the deposition conditions in terms of temperature and pressure, etc.

The DLNs of the present invention have temperature stability far exceeding that of traditional diamond-like (DLC) materials. Crystalline diamond is stable to approximately 1100° C., upon which graphitization occurs. Quartz has long term thermal stability to 1470° C., and short term thermal stability up to 1700° C. Traditional, non-alloyed diamond-like (DLC) films are stable only to about 600° C. before graphitization occurs. By contrast, the DLN structures used to provide the corrosion and erosion resistant coatings of the present invention have long term stability to 1250° C. and short term stability to 2000° C. Therefore the thermal stability of the DLNs exceeds that of DLCs while preserving the amorphous, diamond-like state.

Further, in the range of from about 600° C. to about 1000° C., the chemical bonds of the carbon matrix of DLN materials partly change from $sp^3$ to $sp^2$. However, the general structure of the nanocomposite and their "diamond-like" properties are preserved. By contrast, under similar conditions, the usual "diamond-like" carbon (DLC) is graphitized and loses its diamond-like properties. In the range of from 400° C. to 500° C. (preferably 430° C.), a reverse transition is observed, whereby the ratio of $sp^3$ to $sp^2$ is increased. It is believed that a varying percentage of the carbon in the DLNs is $sp^3$ bonded carbon.

The density of the C—H and Si—O two network DLN varies from about 1.8 to about 2.1 g/cm³. The rest of the space is taken up by a random network of nanopores with diameters varying from about 0.28 to about 0.35 nm. The nanopore network does not form clusters or micropores. The properties of the two network DLN may then be tailored by adding dopant. The dopants fill the nanopore network in a random fashion, eventually resulting, at a certain dopant concentration, in an additional network without clusters or microcrystalline grains, even at concentrations as high as 50 atomic %. At concentrations below about 10 atomic %, the dopants are distributed as separate atoms in the nanopores of the diamond-like matrix. The average distance between dopant atoms in this quasi-random structure can be controlled by the concentration of the dopant. When the relative concentration of the dopant element or compound reaches about 20–25 atomic %, the dopants form the third (Me—

Me) network in the DLN structure as shown in FIG. 1(C), resulting in a material with diamond-like mechanical and chemical properties.

In the intermediate concentration range, where the dopant concentration is from about 10 to about 20 atomic %, the dopants form a fragmented, random network, without true network-like connectivity. The electronic properties of the fragmented dopant "network" depend strongly on external mechanical loading, pressure and electromagnetic fields. The Me-DLNs with dopant concentrations in the range of from about 1 to about 20 atomic % are ideal use as smart materials and sensors. "Smart" materials are understood to be materials that not only sense an external stimulus, but also can react and make appropriate adjustments in response.

The electrical properties of the DLN structures of the present invention can be continuously varied over a wide magnitude (at least 18 orders) from a purely dielectric material to a metallic state while preserving and improving the properties of the DLN state. A transition to a superconducting state, with the absence of electrical resistivity, is observed at low temperatures for certain three-network nanocomposite networks.

Another advantage of the DLNs of the present invention is their relative hardness and durability. The DLNs, especially the metal doped DLNs combine high microhardness with high elasticity. The microhardness values of the DLNs of the present invention range from about 6 to about 30 GPa.

The DLNs may be synthesized via co-deposition by clusterless beams of ions, atoms or radicals of the relevant elements, where the mean free path of each particle species exceeds the distance between its source and the growing particle film surface, and each beam contains particles of well-defined energy. Carbon-containing particle beams can be produced by plasma discharge in a plasmatron and extracted as charged particles by a high-voltage field in a vacuum chamber and directed onto the substrate. At least 50% of the carbon-containing particles have kinetic energy above about 100 eV. The temperature of the substrate during growth should not exceed 500° C.

Figure 4:
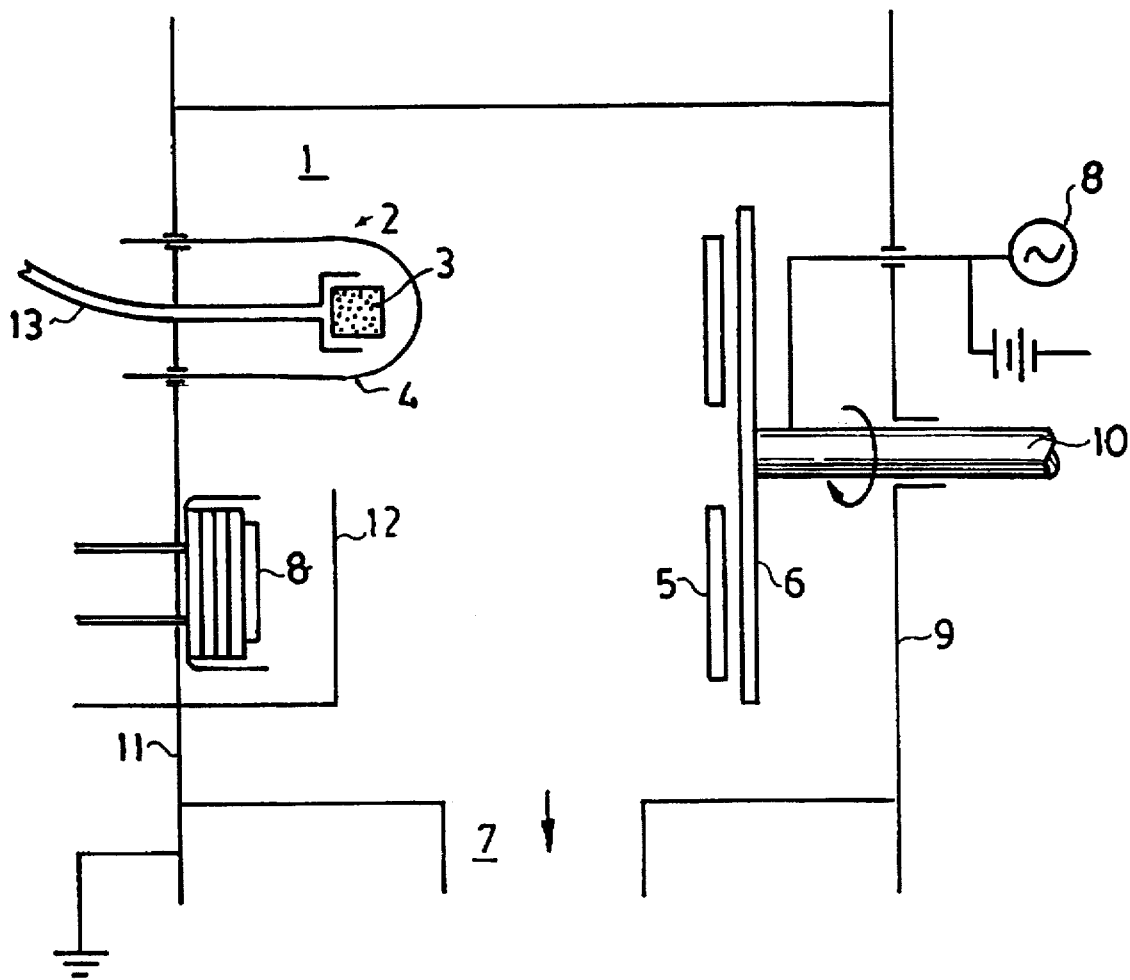
FIG. 4 is a schematic diagram detailing a preferred DLN fabrication and deposition chamber.

FIG. 4 shows one preferred embodiment of the coating chamber used for the DLN coating deposition process. A vacuum deposition chamber 1 is provided to coat a substrate sample. A precursor inlet system 13, comprises a metal tube and a porous ceramic material 3 through which a liquid precursor, preferably a polysiloxane, is injected. The precursor inlet system 13 is shown incorporated into the chamber through the chamber base plate 11. The thermocathode 2 comprises a resistively heated thoriated tungsten filament 4. Substrates 5 to be coated with DLN film are attached to the substrate holder 6. The power supply 8 is used for biasing the substrates (DC or RF). In practice the system is "pumped down" using normal vacuum pump down procedures. A gate valve (not shown) located on port 7 is closed and the system is backfilled with dry air, nitrogen or argon until the chamber reaches atmospheric pressure. The door of the chamber, 9, is then opened and substrate to be coated 5 are attached to the substrate holder 6 using any of many possible methods (spring clip, screw, clamp, etc.). Special fixtures may be required for substrates of special shapes. The substrate holder is designed in a way that it will also hold a cylinder sample (not shown), which, in operation, rotates both about the axis of the central drive shaft 10, and its own axis which is perpendicular to 10. In this way, the axis of the cylinder would be perpendicular to the axis of 10.

When the substrates are loaded, the door of the chamber is closed, the chamber evacuated, and the gate valve opened to bring system pressure down to at least $10^{-5}$ to $10^{-6}$ Torr, which is the desired range of system base pressure. When the above base pressure is achieved, argon gas is introduced into the chamber via a needle valve or mass flow controller, until the chamber pressure reaches approximately $5\times10^{-5}$ to $1\times10^{-3}$ Torr, preferably about $1-3\times10^{-4}$ Torr. The filament current, the filament bias and the electromagnet power supply are then switched on. The filament current is the current that passes through the thermocathode (also called the filament or the cathode). The filament bias is the constant floating voltage applied to the filament (approximately $-150$ V in relation to ground). Plasma current is measured as the current between the filament and the base plate or ground. This voltage provides the field that moves electrons emitted by the filament to the base plate 11. The electromagnet power supply provides current to the electromagnet, which creates a magnetic field that results in the electron path becoming a spiral, increasing the electron path length and improving the probability of collisions between the electrons and the vapor molecules created due to precursor evaporation. The substrate bias power supply is concurrently switched on.

Switching on these power supplies results in creation of an argon plasma, which is used to clean the substrates prior to deposition. After the required duration of cleaning, the precursor supply is opened. Precursor flow is controlled via a needle valve and occurs due to the difference in pressure between the chamber and the outside atmosphere. When precursor flow and vaporization in the chamber has stabilized, the argon gas flow is turned off. The ionized precursor vapors form a stable plasma, ions from which are accelerated towards the substrate holder due to the substrate bias. Thus, deposition of DLN film onto the substrate occurs.

Co-deposition of a dopant material is carried out as follows. Argon flow to the magnetron is commenced and the magnetron 8 is switched on after the base pressure has been reached. A shutter 12 is used to prevent deposition while the substrate is cleaned via sputtering. When cleaning has been accomplished, the shutter is opened and sputtering is carried out at the desired power level. This may occur prior to commencement of DLN film deposition, during DLN film deposition, after DLN film deposition, or intermittently during DLN film deposition, depending on what kind of film structure and composition to be deposited are desired. Using DC or RF sputtering, materials of all kinds (metals, ceramics, alloys, etc.) can be used for co-deposition.

The growth conditions for nanocomposite films are the following, with reference to FIG. 4. The pressure in the deposition chamber 1 should not exceed $10^{-3}$ torr, with the pressure in the active zone of the plasma generation 2, in the range from about $1.0\times10^{-3}$ to about $5.0\times10^{-2}$ torr. The temperature of the substrate should not exceed about 200° C. with the temperature of the cathode filaments being in the range from about 2100° to about 2950° C. The current in the cathode filament is from about 70 to about 130 A, with the voltage across the filament being from about 20 to about 30 V. The voltage with respect to the ground is from about 70 to about 130 V with the plasma current being from about 0.5 to about 20.0 A. The voltage of the substrate holder is from about 0.1 to about 5.0 Kv, with all the carbon-containing and Si-containing species having kinetic energy in the range of from about 100 to about 1200 eV and from about 25 to about 300 eV respectively. The metal beams consist of free atoms or monatomic ions. The kinetic energy of the metal atoms/ions does not exceed from about 25 eV. With a precursor flow rate from about 0.5 to about 5.0 cc/hour, the growth rate of the DLN is from about 0.1 to about 2.0 micrometers/hour.

The preferred range of operation for most applications is a pressure of about $1-3\times10^{-5}$ Torr, a plasma current of about 1 amp., a filament current of from about 60 to about 75 amp., a substrate voltage of from about 600 to about 1000 V DC, or forward power of about 100 W in RF mode. The preferred frequency for RF mode is from about 90 to about 300 KHz. The preferred magnetron power depends on the type of material, composition and structure desired for the DLN coating.

Figure 2:
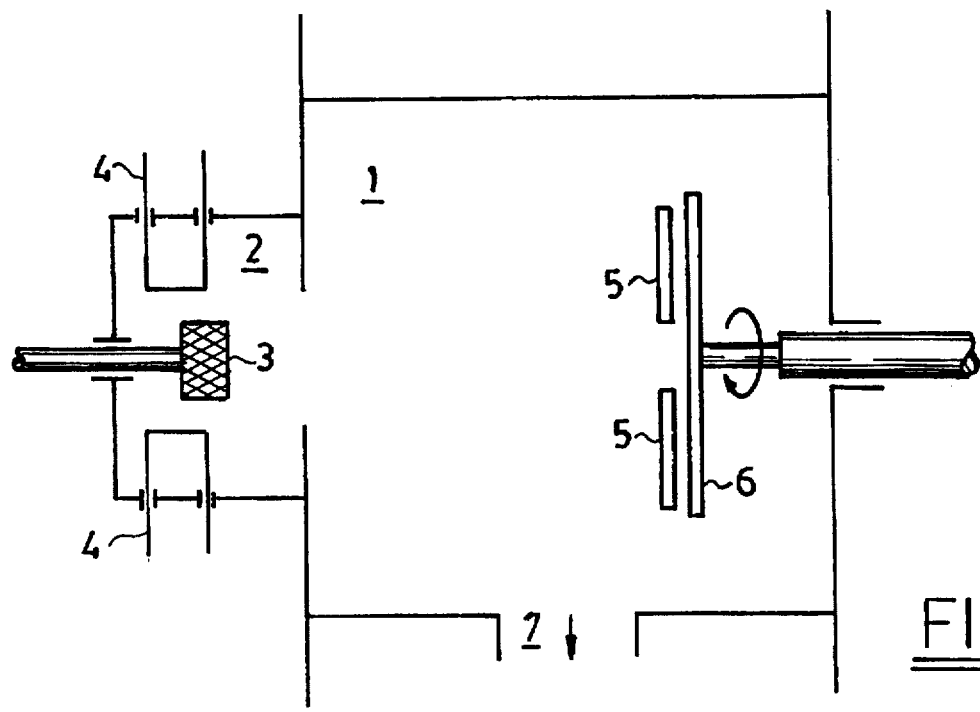
FIG. 2 is a schematic diagram detailing the main method of fabrication of the DLN corrosion resistant coatings.

In a further preferred embodiment, a preferred method of deposition uses a plasma discharge in a triode plasmatron, as shown schematically in FIG. 2, with the plasma energy density above about 5 Kwh/gram-atom of carbon. The charged particles are extracted by a high voltage field in the vacuum chamber and directed onto the substrate. It is preferable that the potential of the substrate holder is from about −0.3 to about +5.0 Kv, and most preferably 1.0+/−0.2 Kv, and varying with a frequency in the range of from about 0 to about 25 Mhz for DC and from about 90 to about 300 KHz for RF. The ratio of the electron emission to the carbon precursor flow in the plasmatron is from about 0.5 to about 1.5 electrons per particle.

Organosilicon compounds, such as siloxane, are preferred precursors for C, H, Si and O. One preferred organosilicon compound is polyphenylmethylsiloxane, containing 1 to 10 Si atoms. The high boiling point siloxanes may be introduced directly into the active plasma region through a porous ceramic or metallo-ceramic (3 in FIGS. 2 and 3) which is heated via radiation thermocathodes 4. The photon and electron emission of the thermocathodes affect the evaporation, fragmentation and ionization of the precursor molecules on the surface of the ceramic, which thereby functions as an ion source for the plasma generator. An alternative method for injection of the siloxane precursors is to use direct injection from a diffusion pump.

The formation of dopant-containing beams may be realized by any one of, or combination of, the following methods: 1) thermal evaporation; 2) ion-sputtering; 3) ion beams. The dopant-containing beams are directed onto the growing film surface through the vacuum chamber to exclude interparticle collisions in the deposition chamber itself. Substrates are placed in an adjacent chamber on a rotating substrate holder, (for example a drum) which ensures double rotary motion, said adjacent chamber being connected to the plasma generation chamber by an opening for the emission of the atomic or ionic beams, as shown schematically in FIG. 2. Alternatively, the plasma generation may be carried out within the chamber containing the substrates (FIG. 4). A DC or a radio frequency potential is generally applied to the substrates during the deposition process. No external substrate heating is required. The substrate holder may be designed specifically to hold parts of different shapes such as cylinders, as would be apparent to one skilled in the field.

Useful variation of the above described methods for deposition of DLN films include the use of sputtered silicon and oxygen gas as precursors for the Si and $O_2$, the use of sputtered carbon and hydrogen or hydrocarbon gas used as carbon and hydrogen precursors, or any combination thereof.

Figure 3:
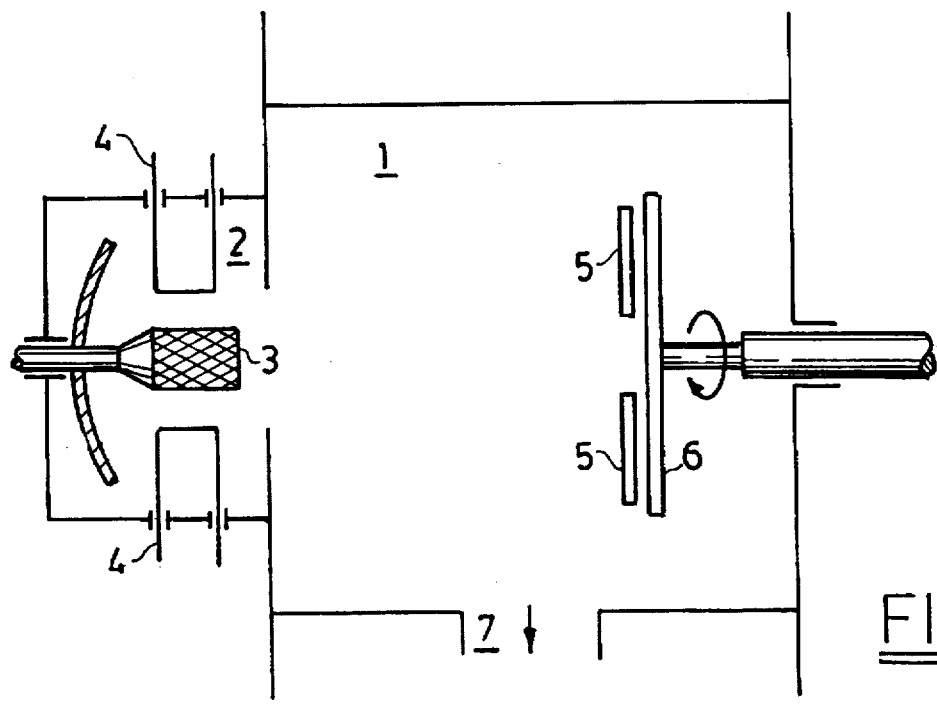
FIG. 3 is a schematic diagram detailing the methods of fabrication of DLN corrosion resistant coatings using reflected beam flow.

For deposition on non-conducting substrates, such as plastic, a method whereby a flow of neutral radicals is reflected from a high voltage target and directed to the substrate as shown schematically in FIG. 3. The process employs depositions similarly to those shown in FIG. 2, except that a reflecting electrode is used to generate a neutral beam. This process eliminates surface damage of the substrate resulting from charged and/or fast particles impinging on the substrate during growth.

A preferred method for depositing ultra-thin dielectric DLN films comprises ion bombardment (e.g. $Ar^+$ or $K^+$ with energy in the range of from about 30 to about 150 eV) through a vacuum chamber which has been backfilled by siloxane vapor (about $3\times10^{-4}$ torr). This results in a self-stabilized growth of a nanocomposite film, with the maximum thickness controlled by the maximum tunneling distance for the relaxation of the charge of the absorbed radicals.

Extremely uniform and nonporous ultra-thin dielectric films may be deposited according to the present invention. The thickness of the deposited DLN coating has no theoretical limit. Existing technology and available equipment have allowed atomic-scale composite films and coating thicknesses typically in the range from about 1 μm to about 10 μm. According to this method, a film thickness in the range from about 6 to about 8 nm may be deposited, with a deposited film thickness of from about 3 to about 5 nm being also achievable.

Therefore, the above-described flexible coatings of the present invention may be deposited on the selected substrate in thicknesses ranging from a few nanometers to a few microns, preferably from about 20 nm to about 12 microns, depending only on the desired application of the coated substrate. The deposition may be tailored or "tuned" to meet the properties required for a particular application. The random interpenetrating of the two- or three-network DLNs guarantee uniform strength of the structures in all directions. The structures are free of micropores even at thicknesses of 80 Angstroms (8 nm). The DLNs are therefore extremely stable and possess unique combinations of chemical, mechanical, electronic, and superconducting properties.

Many uses for the DLN coatings of the present invention exist, including but not limited to the coating of metals and non-metals, surgical instruments, biomedical devices and implants, decorative metals, metals and non-metals used as building materials, and any substrates which are vulnerable to corrosive attack such as those listed within the present specification. The following examples serve only to further illustrate aspects of the present invention and should not be construed as limiting the invention.

EXAMPLES

A variety of comparative metal and non-metal based coatings were prepared and used to coat substrates of various materials to determine relative corrosion-resistance performance and other properties. Within the category of DLN coatings, a wide range of films in the DLN family of coatings were deposited on various substrates in order to demonstrate the versatility of this approach. The film compositions included non-metal, two-network DLNs (undoped) and DLNs doped with hafnium (Hf), chromium (Cr), tungsten (W), titanium (Ti), tantalum (Ta), zirconium (Z), titanium nitride, zirconium nitride and hafnium nitride. A schematic of the deposition chamber is shown in FIGS. 2–4. Magnetron sputtering was used for all electrically conductive targets. Substrates on which DLN coatings were deposited included stainless steel (401), aluminum (6061), high density polyethylene (HDPE), polycarbonate, polyimide, Teflon™ (sheets and films), polyurethane, alumina, and silicon. Standardized adhesion tests ASTM D3359B were carried out for Teflon and HDPE. Qualitative evaluations indicated excellent adhesion in all cases.

Square polished coupon samples of aluminum 6061 measuring 2"×2"×¼" were coated with a three micron thick Zr-DLN coating. Several coupons were cleaned with alcohol and mounted in the coating chamber on the substrate holder plate using metal clips. The chamber was closed and pumped down to $3\times10^{-5}$ Torr. Argon gas flow was started and increased until the chamber pressure reached $1.5\times10^{-4}$ Torr. The magnetron shutter was closed and the magnetron power supply was switched on. Ion cleaning of the coupon began at a power level of 200 W. After 20 minutes of cleaning, the filament current was turned on and increased to 65 amps while the filament bias voltage was −158 V and electromagnet current was 250 milliamps. Substrate RF bias was switched on to 100 W forward power at a frequency of 210 kHz. Substrate holder rotation was started and maintained at 7 rpm. After 10 minutes, of plasma cleaning of the substrate (coupon), the precursor needle valve was opened to a setting of 3 cc/hour. After about 5 minutes, the argon gas flow was stopped. A plasma current of about 1 amp was obtained. Concurrently, the magnetron shutter was opened to a setting of 450 W. Substrate load power was about 80 W. After about 4 hours, the precursor valve was closed, and the power supplies switched off. The chamber and substrates within were allowed to cool. The chamber was then back-filled with nitrogen and the DLN coated infrared windows removed from the substrate holder.

Example 1–9

Salt Fog Exposure

DLN and doped-DLN coatings were tested according to the ASTM B117 salt fog test. (Examples 1–4). For comparisons, uncoated steel and aluminum samples were similarly tested (Comparative Examples A–B).

Comparative Example A

An uncoated aluminum sample was subjected to 72 hour salt spray per ASTM B117. After testing, the sample had a general tarnished appearance with some white corrosion products visible.

Example 1

A samples of aluminum was coated with an approximately 3 micron Hf-DLN coating. After testing, no corrosion or degradation of coated surface was visible.

Example 2

A sample of aluminum was coated with an approximately 3 micron DLN coating. After testing, no corrosion or degradation of the coated surface was visible.

Comparative Example B

A sample of uncoated stainless steel was subjected to 72 hour salt spray per ASTM B117. After testing, scattered rust spots were visible.

Example 3

A sample of stainless steel was coated with an approximately 3 micron Hf-DLN (doped) coating. After testing, several rust streaks were visible on the coated surface emanating from the edges. This was believed to be a result of flow of corrosion products from uncoated areas.

Example 4

A sample of stainless steel was coated with an approximately 3 micron DLN coating. After testing, slight staining was visible on the coated surface. This was believed to be a result of flow of corrosion products from uncoated areas.

Comparative Example C

Figure 5A:
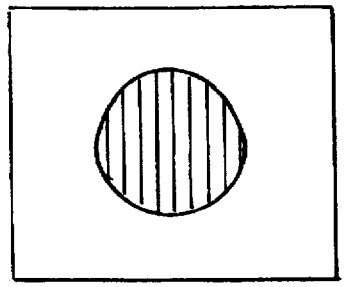
FIGS. 5A–5F show a series of drawings representing the results of abrasion testing on DLN coated and uncoated samples.

A sample of aluminum was subjected to falling sand abrasion test per ASTM D968, Method A. The results of the test are noted in FIG. 5A.

Example 5

Figure 5B:
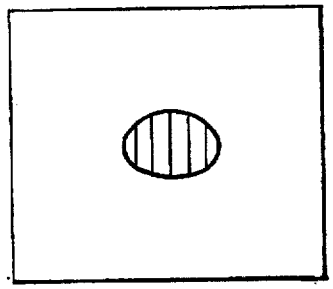

A sample of aluminum coated with an approximately 3 micron thick coating of Hf-DLN was subjected to falling sand abrasion test per ASTM D968, Method A. The results of the test are noted in FIG. 5B.

Example 6

Figure 5C:
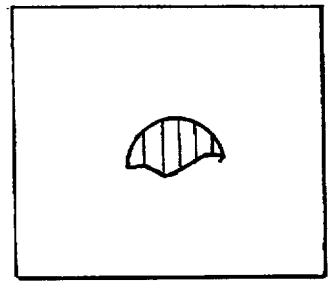

A sample of aluminum coated with an approximately 3 micron thick coating of DLN was subjected to falling sand abrasion test per ASTM D968, Method A. The results of the test are noted in FIG. 5C.

Comparative Example D

Figure 5D:
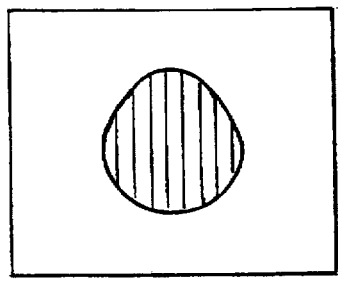

A sample of stainless steel was subjected to falling sand abrasion test per ASTM D968, Method A. The results of the test are noted in FIG. 5D.

Example 7

Figure 5E:
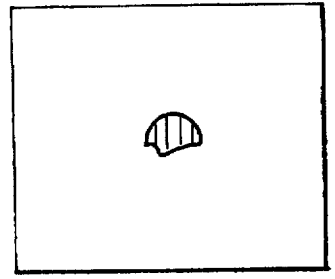

A sample of stainless steel coated with an approximately 3 micron thick coating of Hf-DLN was subjected to falling sand abrasion test per ASTM D968, Method A. The results of the test are noted in FIG. 5E.

Example 8

Figure 5F:
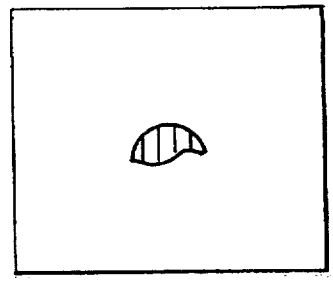

A sample of stainless steel coated with an approximately 3 micron thick coating of DLN was subjected to falling sand abrasion test per ASTM D968, Method A. The results of the test are noted in FIG. 5F.

In all instances of Examples 5–8 and Comparative Examples C–D, the imprint shown in FIGS. 3A–3F is the size and shape of the erosion area on the tested specimens (2"×2"). The volumes listed under FIGS. 6A–6F is the volume of sand used for the test.

Data from the testing of Examples 5–8 and Comparative Examples C–D are further presented in Table 1. For coated specimens, the volume of sand required to abrade through the 3 micron coating was determined. The determination of 'wear-through' is made by the unaided eye. For uncoated specimens, since there was no way to measure the depth of the abraded area, the total area of erosion by 2 liters of sand was taken as a qualitative measure of the extent of abrasion. See FIGS. 5A–5F. Following the testing, the erosion area on uncoated aluminum was approximately 3 times that seen on the DLN coated aluminum for the same sand volume. The erosion area on uncoated steel was approximately 6 times that seem on the DLN coated steel for the same sand volume. The erosion test was done at three locations on each sample.

TABLE 1

Comparative Erosion Resistance

| Ex. # | Samp. | Liters of Sand Area 1 | Area 2 | Area 3 | Erosion Resistance Area 1 | Area 2 | Area 3 | Avg. l/μ |
|---|---|---|---|---|---|---|---|---|
| C | Al | — | 2.00 | — | — | 0.17 | — | 0.17 |
| 5 | Al/Hf-DLN | 1.00 | 1.25 | 1.10 | 0.33 | 0.42 | 0.37 | 0.37 |
| 6 | Al/DLN | 1.50 | 1.50 | 1.40 | 0.5 | 0.5 | 0.47 | 0.49 |
| D | Steel | — | 2.00 | — | — | 0.20 | — | 0.20 |
| 7 | Steel Hf-DLN | 3.00 | 2.65 | 2.65 | 1.00 | 0.88 | 0.88 | 0.92 |
| 8 | Steel/DLN | 1.75 | 2.00 | 1.65 | 0.58 | 0.67 | 0.55 | 0.60 |

Example 9

A sample of Teflon™ was coated with a three micron thick DLN coating, and tested for tape adhesion per ASTM D3359, Method B. The sample, after testing, exhibited an adhesion rating of 2B, 2B and 3B for three areas tested. A rating of 5B is the highest possible rating, where no flaking occurs from the surface of a cross cut area. 0B is the rating where greater than 65% of the coating was removed.

Example 10

A sample of HDPE was coated with a three micron thick DLN coating, and tested for tape adhesion per ASTM D3359, Method B. The sample, after testing, exhibited an adhesion rating of 5B, 5B and 5B for three areas tested. A rating of 5B is the highest possible rating, where no flaking occurs from the surface of a cross cut area. 0B is the rating where greater than 65% of the coating was removed.

Examples 11–26

Exposure to Hot Alkali

Corrosion resistance studies were carried out on metal-doped DLN coatings on silicon substrates using a variety of chemical agents and metal dopants. The results are listed in the following Table 2.

TABLE 2

Chemical Stability of Me-DLN in 35% KOH at 100–108° C. Example Number in ( )

| Composit'n | Surface resistivity[2] (Ωcm) | Thickness (nm) | Time (min) | Surf |
|---|---|---|---|---|
| (11) W-DLN | 190 | 3000 | 90 | a |
| (12) W-DLN | 40 | 640 | 90 | b |
| (13) W-DLN | 21 | 700 | 90 | a |
| (14) W-DLN | 19 | 740 | 90 | a |
| (15) W-DLN | 10 | 1000 | 90 | a |
| (16) W-DLN | 3.6 | 3000 | 90 | a |
| (17) Cr-DLN | 16 | 1100 | 90 | a |
| (18) Cr-DLN | 422 | 600 | 90 | a |
| (19) NiCr-DLN | 106 | 750 | 90 | a |
| (20) Cu-DLN | $1.7 \times 10^3$ | 800 | 90 | c |
| (21) Mo-DLN | 733 | 750 | 90 | d |
| (22) Mo-DLN | 1000 ($10^4$) | 1100 | 90 | e |
| (23) Mo-DLN | 0.5 | 400 | 30 | f |
| (24) Ta-DLN | 42 | 200 | 90 | g |
| (25) Zr-DLN | 2.1 | 675 | 90 | g |
| (26) Hf-DLN | 5.6 | 340 | 90 | g |

Surf = Surface Appearance
a = no change
b = pitting
c = surface darkening from 50 min.; no etching
d = etching from 60 min.
e = etching from 70 min.
f = etching from 10 min.
g = etching from 60 min.

Resistance to corrosion seemed to depend not only on the dopant used, but the amount of dopant which is indirectly indicated by surface resistivity. Corrosion resistance also depends on the film thickness. While very thin films could be used as molecular sieves, for corrosion protection of a substrate using DLN, it is believed that a film at least 1 micron thick must be used.

Examples 27–66

Exposure to Acid Solutions

Corrosion testing was carried out using acidic solutions on Me-DLN films having the compositions shown in the following Table 3.

TABLE 3

| Example Number | Composition | Acid |
|---|---|---|
| 27 | W-DLN | 10% HCl |
| 28 | W-DLN | 10% $H_2SO_4$ |
| 29 | W-DLN | 10% $HNO_3$ |
| 30 | W-DLN | 10% HCl+$HNO_3$ |
| 31 | W-DLN | 35% KOH |
| 32 | Cr-DLN | 10% HCl |
| 33 | Cr-DLN | 10% $H_2SO_4$ |
| 34 | Cr-DLN | 10% $HNO_3$ |
| 35 | Cr-DLN | 10% HCl+$HNO_3$ |
| 36 | Cr-DLN | 35% KOH |
| 37 | NiCr-DLN | 10% HCl |
| 38 | NiCr-DLN | 10% $H_2SO_4$ |
| 39 | NiCr-DLN | 10% $HNO_3$ |
| 40 | NiCr-DLN | 10% HCl+$HNO_3$ |
| 41 | NiCr-DLN | 35% KOH |
| 42 | Cu-DLN | 10% HCl |
| 43 | Cu-DLN | 10% $H_2SO_4$ |
| 44 | Cu-DLN | 10% $HNO_3$ |
| 45 | Cu-DLN | HCl+$HNO_3$ |
| 46 | Cu-DLN | 35% KOH |
| 47 | Mo-DLN | 10% HCl |
| 48 | Mo-DLN | 10% $H_2SO_4$ |
| 49 | Mo-DLN | 10% $HNO_3$ |
| 50 | Mo-DLN | HCl+$HNO_3$ |
| 51 | Mo-DLN | 35% KOH |
| 52 | Ta-DLN | 10% HCl |
| 53 | Ta-DLN | 10% $H_2SO_4$ |
| 54 | Ta-DLN | 10% $HNO_3$ |
| 55 | Ta-DLN | HCl+$HNO_3$ |
| 56 | Ta-DLN | 35% KOH |
| 57 | Zr-DLN | 10% HCl |
| 58 | Zr-DLN | 10% $H_2SO_4$ |
| 59 | Zr-DLN | 10% $HNO_3$ |
| 60 | Zr-DLN | HCl+$HNO_3$ |
| 61 | Zr-DLN | 35% KOH |
| 62 | Hf-DLN | 10% HCl |
| 63 | Hf-DLN | 10% $H_2SO_4$ |
| 64 | Hf-DLN | 10% $HNO_3$ |
| 65 | Hf-DLN | HCl+$HNO_3$ |
| 66 | Hf-DLN | 35% KOH |

No corrosion or deterioration was observed after exposure of the coated substrates (about 1 micron thick DLN coatings) at room temperature for 24 hours to the chemical agents shown above.

Example 67

A variety of doped and non-doped DLN coatings were deposited on substrates made from steel, alumina and silicon. The following Table 4 shows the derived corrosion performance of DLN and doped-DLN coatings.

TABLE 4

| Test Conditions | DLN Film Thickness (nm) | Time Until Corrosion |
|---|---|---|
| 5% HCl | 5 | 30–40 sec |
| 5% HCl | 8 | 80–100 sec |
| 5% HCl | 100 | >100 hrs |
| 10% HCl | 300 | >400 hrs |
| HCl gas, 1200° C. | 200 | >3 hrs |
| 5% HF | 100 | 100 sec |
| 5% HF | 300, W-DLN | >100 hrs |
| Salt Water (Black Sea) | 200 | >800 hrs |

Example 68

Thermal Stability of DLN Films

DLN films were tested for stability under high annealing temperatures, both in air and in vacuum. Thermal stability and maintained adhesion is required for the protection of weapon systems which undergo severe thermal shock and cycling under operating conditions. No film delamination was observed following the thermal testing that was carried out on DLN films. Analyses were carried out via visual observation, mechanical property determinations on annealed films and FTIR spectroscopy to determine changes in film structure.

Annealing at 400° C. in air for 9 hours followed by 600° C. for 1 hour in vacuum did not change the film structure or degrade its properties.

Example 69

Mechanical Properties of DLN Films

High hardness and mechanical modulus measurements were obtained on 9 different compositions of DLN and doped-DLN films. Measurements were carried out using a nanoindenter (Nanoinstruments, Knoxville, Tenn.). Hardness ranged from about 6 to about 21 GPa. Elastic modulus of approximately 200 GPa was achieved, which matches approximately the modulus of steel. Harness/modulus degradation in the films was minimal after exposure to 500° C.

Many other modifications and variations of the present invention are possible to the skilled practitioner in the field in light of the teachings herein. It is therefore understood that, within the scope of the claims, the present invention can be practiced other than as herein specifically described.

We claim:

1. A corrosion resistant material made from a substrate susceptible to corrosion and a corrosion resistant coating, said coating made from a class of diamond-like solid state materials formed from interpenetrating networks, said networks comprising a first network of diamond-like carbon stabilized by hudrogen, a second silicon network stabilized by oxygen and, optionally, at least one network of dopant elements, or dopant compounds containing elements from groups 1–7b and 8 of the periodic table.

2. The material according to claim 1 wherein the carbon, hydrogen, silicon and oxygen are obtained from the decomposition of an organosiloxane having from about 1 to about 10 silicon atoms.

3. The material according to claim 2 wherein the organosiloxane is polyphenylmethylsiloxane.

4. The material according to claim 1 wherein the carbon content is from about 40 wt. % to about 98 wt. %.

5. The material according to claim 1 wherein the carbon content is from about 50 wt. % to about 98 wt. %.

6. The material according to claim 1 wherein the carbon to silicon weight ratio is from about 2:1 to about 8:1.

7. The material according to claim 1 wherein the silicon to oxygen weight ration is from about 0.5:1 to about 3:1.

8. The material according to claim 1 wherein the dopant elements are selected from the group consisting of B, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag, and Au.

9. The material according to claim 1 wherein the carbon content of the solid state material is at least 40 atomic % of the coating, the hydrogen content is up to about 40 atomic % of the carbon, and the sum of the silicon, oxygen and dopants together is greater than about 2 atomic % of the coating.

* * * * *